United States Patent [19]
Rich, Jr.

[11] Patent Number: 4,783,871
[45] Date of Patent: Nov. 15, 1988

[54] WATER POWERED TOOTHBRUSH

[76] Inventor: Joseph Rich, Jr., R.D. 2, 177-B, Cobblewood Rd., Blairstown, N.J. 07825

[21] Appl. No.: 10,465

[22] Filed: Feb. 3, 1987

Related U.S. Application Data

[63] Continuation-in-part of Ser. No. 730,115, May 30, 1985, abandoned.

[51] Int. Cl.⁴ .............................................. A46B 13/02
[52] U.S. Cl. .................................... 15/23; 15/24
[58] Field of Search ............ 15/23, 24, 28, 29, 97 R; 415/202, 203, 92; 366/250

[56] References Cited

U.S. PATENT DOCUMENTS

| | | | |
|---|---|---|---|
| 1,045,204 | 11/1912 | Simons | 415/92 |
| 1,133,907 | 3/1915 | Allan | 15/24 |
| 1,228,897 | 6/1917 | Frame | 15/24 |
| 2,172,195 | 9/1939 | Elson | 15/24 |
| 2,283,314 | 5/1942 | Ckola | 15/24 |

FOREIGN PATENT DOCUMENTS

| | | | |
|---|---|---|---|
| 262496 | 6/1964 | Australia | 15/23 |
| 552349 | 6/1932 | Fed. Rep. of Germany | 15/24 |
| 353060 | 10/1937 | Italy | 15/24 |

*Primary Examiner*—Edward L. Roberts
*Attorney, Agent, or Firm*—Evelyn M. Sommer

[57] ABSTRACT

A water powered rotary toothbrush is provided which includes a housing having inlet and outlet ports and a rotatable center shaft. The rotatable center shaft has one end provided within the housing. A paddle wheel is located in the housing and is fixedly attached to the shaft near the one end thereof. The opposite end of the shaft extends out of the housing and has removably attached thereto a rotary brush element. Water is introduced into the housing through the inlet port where it is directed against the paddle wheel causing it and the center shaft to which it is fixedly attached, to rotate. The rotation is translated to the brush element which likewise rotates. Excess water is removed through the outlet port.

7 Claims, 2 Drawing Sheets

WATER POWERED TOOTHBRUSH

RELATED APPLICATIONS

This application is a continuation-in-part of U.S. application Ser. No. 730,115, filed May 30, 1985, now abandoned.

BACKGROUND OF THE INVENTION

1. Field of the Invention

The present invention relates generally to a water powered toothbrush and, more particularly, to such a toothbrush which includes a removable rotary brush element capable of rotating in either direction. The water powered toothbrush of the present invention uses a minimum amount of water.

2. Background of the Invention

Toothbrushes which include water jets have been used for a number of years. Examples of such toothbrushes include the devices described in U.S. Pat. No. 1,097,122 which issued on May 19, 1914 to C. O. Engstrom for Tooth Brush; U.S. Pat. No. 1,479,275 which issued on Jan. 1, 1924 to H. W. Beil for Toothbrush; U.S. Pat. No. 2,303,667 which issued on Dec. 1, 1942 to A. F. Taborski for Toothbrush; U.S. Pat. No. 2,516,195 which issued on July 25, 1950 to C. H. Finton for Fountain Toothbrush; U.S. Pat. No. 2,855,619 which issued on Oct. 14, 1958 to H. M. Graham for Toothbrush; U.S. Pat. No. 3,135,989 which issued on June 9, 1964 to M. Gatti for Toothbrush with Automatic Spraying of the Bristles; U.S. Pat. No. 4,175,879 which issued on Nov. 27, 1979 to P. Molinari for Toothbrush; and U.S. Pat. No. 4,239,409 which issued on Dec. 16, 1980 to L. Osrow for Brush Assembly with Pulsating Water Jet Discharge. Each of these toothbrushes use the introduced water for rinsing or flushing rather than for actually powering the brush itself.

U.S. Pat. No. 1,133,907 which issued on Mar. 30, 1915 to H. Allan for Rotary Tooth Brush; U.S. Pat. No. 2,283,314 which issued on May 19, 1942 to J. L. Okola for Hydio Dental Brush and Italian patent No. 353,060 which issued on Oct. 4, 1937 to F. Bianco provide tooth brushes which rotate only in one direction. Further, the Allan and Bianco patents have shields adjacent to the brush head which would necessarily hamper one in brushing ones' teeth. Still further, the Allan and Okola patents provide a unit which permits water to reach the brushes head thereby requiring relatively more water to make these brushes perform properly.

Australian Pat. No. 262,496 which published on June 18, 1964 to Pearson for the Water Driven Rotary Toothbrush permits by the use of twin turbine of opposing blades rotation of the brush head in either direction. The rotation in either direction needs an additional mechanical assembly such as an oscillating inlet injector which applies pressure alternatively to each turbine or a plunger valve. Further, this patent provides for the diverting of water to the brush head (for rinsing purposes) which diversion necessarily requires relatively more water.

SUMMARY OF THE INVENTION

It is a primary object of the present invention to provide a water powered toothbrush which relies on water pressure to assist in effecting the brushing action.

It is another object of the present invention to provide such a toothbrush which can also be used for gum massage.

It is still another object of the present invention to provide such a toothbrush which can accommodate removable rotary brush elements.

It is still yet another object of the present invention to provide such a toothbrush which can readily reverse the direction of rotation of the toothbrush.

It is still further another object of the present invention to provide such a toothbrush which minimizes the amount of water needed to perform effectively.

To the accomplishments of the foregoing objects and advantages, the present invention, in brief summary, comprises a water powered rotary toothbrush which includes a housing having a rotatable center shaft provided within the housing. A paddle wheel is fixedly attached to the shaft near one end thereof. The opposite end of the shaft extends out of the housing and is adapted to have a rotary brush element removable attached thereto. The housing also includes a pair of ports positioned proximate to the paddle wheel. Water may be introduced into the housing through one of the pair of ports and is directed against the paddle wheel causing it and the center shaft to which it is fixedly attached, to rotate. The rotation is translated to the brush element which, likewise, rotates. Either one of the pair of ports can interchangeable be the inlet or outlet port thereby facilitating reversal of the direction of rotation of the brush element.

BRIEF DESCRIPTION OF THE DRAWINGS

The foregoing and still other objects and advantages of the present invention will be more apparent from the following detailed explanation of the invention in connection with the accompanying drawings, wherein.

DETAILED DESCRIPTION OF THE PREFERRED EMBODIMENTS

Figure 1:
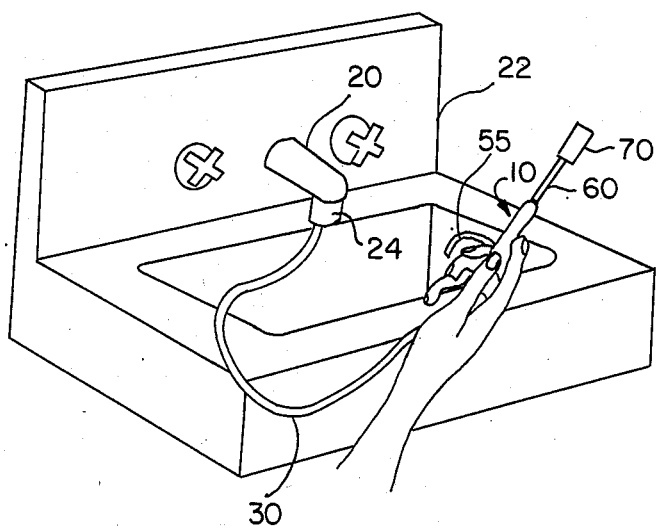
FIG. 1 illustrates the manner in which the water actuated toothbrush of the present invention is to be used.
Figure 2:
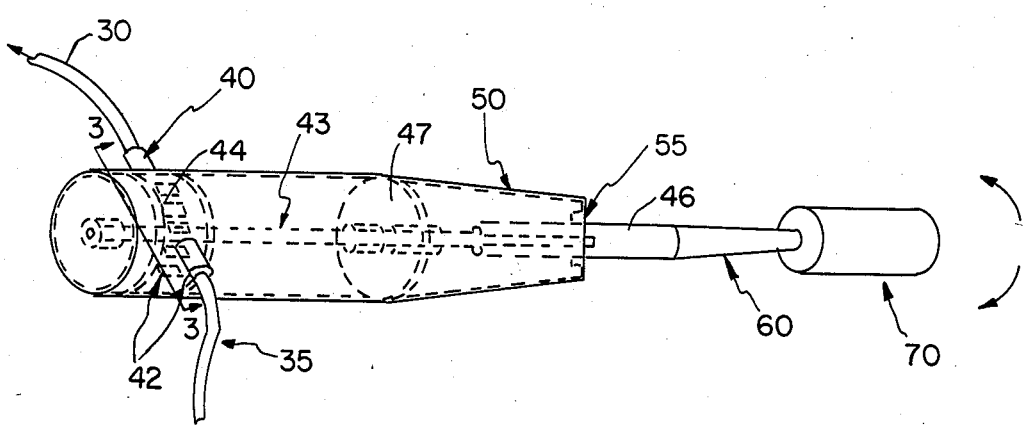
FIG. 2 is a sectional side view of the toothbrush of the present invention.

Referring now to the drawings and, in particular, to FIG. 1 thereof, a water powered toothbrush, identified generally by reference numeral 10, is provided. The toothbrush 10 is adapted to be used in association with a water faucet 20 from a bathroom sink 22, the water from which is used to power the rotary toothbrush 10. The toothbrush 10, which is shown in greater detail in FIG. 2, is connected to the faucet 20 of the sink 22 by a flexible water inlet tube 30 and a faucet connector 24. The faucet connector 24, which is preferably of rubber or another flexible material, is adapted to engage in a water tight manner one end of tube 30 and to fit over the faucet 20 of the sink 22 thereby readily permitting connection of the toothbrush 10 to the faucet 20. The flexible water inlet tube 30 can also be made of rubber or another flexible material which is not corroded by water. Inlet table 30 may have any conventional inside and outside diameters, however it is preferable that the inlet tube have an inside diameter of approximately 0.032 inches and an outside diameter of approximately 3/16 of an inch. Inlet tube 30 connects the toothbrush 10 to the faucet 20 so as to permit water from the faucet to be introduced under pressure, directly into the toothbrush to power same.

As shown in greater detail in FIG. 2, the toothbrush 10 includes a housing 50 having a center shaft 43 with a removable brush element 70 at one end thereof. Water inlet tube 30 is connected by conventional means to the housing 50 at a first or inlet port 40. Preferably, port 40 is sized so as to have inlet tube 30 snugly fit therein, i.e. fit so as to prevent water leakage. A companion second or outlet port 42 is provided on the side of the housing 10, basically directly opposite the inlet port 40. A water drain tube 35 is connected at one end to the outlet port 42, and opposite end of the drain tube is adapted to be placed in the sink 22 or other receptacle for draining excess water from the toothbrush 10. The water drain tube 35 may have any conventional inside and outside diameters, however it is preferable that the outside diameter must be the same or almost the same as the outside diameter of inlet tube 30 and the inside diameter should be slightly larger than that of the inlet tube to effect a ready discharge of water. Accordingly for the preferred inlet tube 30, the water drain tube 35 should also have an outside diameter of approximately 3/16 of an inch and an inside diameter of approximately ⅛ of an inch. Drain tube 35, as inlet tube 30 in part 40, snugly fits in the second or outlet port 42, i.e.. fits in a manner so as to prevent water leakage. By reversing the connections so that the inlet tube 30 is connected to second port 42 and the drain tube 35 is connected to first port 40, second port 42 becomes the inlet port, while first port 40 becomes the outlet port. As explained below, the brush element 70 will rotate in different directions depending on which port is the inlet port (or outlet port). The inside diameter of the ports 40, 42 are basically the same so as to snugly receive the same outside diametered inlet tube 30 or drain tube 35, in the connection shown in FIG. 2. By this construction, the inlet tube and drain tube can be readily interchanged in each port. The actual connector of each tube to either port is not important other than that each tube can be readily interchanged with each port.

The center shaft 43 has a paddle wheel 44 thereon located near one end of the center shaft. The paddle wheel 44 is connected to or readily mounted on the center shaft so as to rotate with the center shaft and is located proximately evenly spaced relative to the first and second ports 40 and 42, respectively. The paddle wheel 44 is fixedly mounted relative to the center shaft 43. Center shaft 43 is supported in the center of the housing 50 by a support disc 47 having a center aperture through which the center shaft 43 passes. The center shaft 43 is supported in housing 50 so as to permit the shaft to rotate in either direction. The other or outward end 46 of the center shaft 43 extends out of the housing and is adapted to receive and be connected to an end 60 of a removable brush element 70. A seal 55 is provided at the one end of the housing 10 about the outward end 46 of the center shaft 43. It will be appreciated that since brush elements 70 are removable, the same toothbrush 10 can be used by different family members, each having their own brush element 70. The brush element 70 can be conventional bristle brushes or of any other type of brush or buffing substances.

Figure 3:
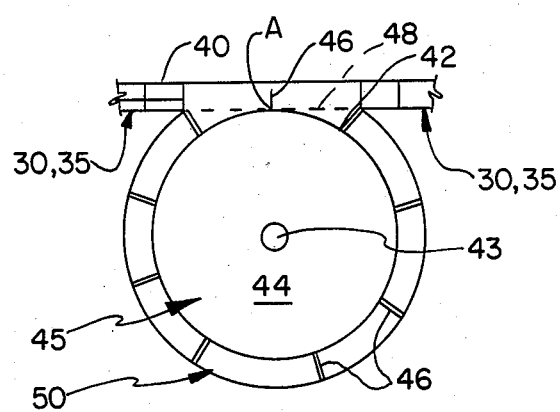
FIG. 3 is a sectional view taken along lines 3—3 of FIG. 2.

Referring to FIG. 3, the paddle wheel 44 on center shaft 43 includes a solid hub 45 and a plurality of paddle legs or extensions 46 which extend from the hub immediately adjacent, but not contacting, the inside of the housing 50. The diameter of the hub 45 is preferable at least two times greater than the radial extent or height of each paddle leg 46.

First and second port 40 and 42, respectively, are basically directly aligned and opposite to each other. Each port is approximately the same distance from the paddle wheel 44. The ports 40, 42 are positioned in a direct line with only paddle legs 46 therebetween so that water directed through one port is directed to strike only one paddle leg 46, and not hub 45, and is emitted out of the housing 50 through the other port. Further, the point A at which each paddle leg 46 contacts hub 45 is aligned with the lower limit of ports 40, 42 when the leg is in the vertical most position shown in FIG. 3. By not having some of the forces of the water dissipated by striking hub 45, relatively less water is needed to turn the paddle wheel 44. To assure that hub 45 is not directly struck by water forced through the inlet port 40 or 42, the circumference of the hub 45 is below the direct path of the water between ports 40 and 42. Further, by the solid construction of hub 45, water is prevented from flowing into the housing 50 and especially towards head 70.

It will be appreciated that the toothbrush 10 of the present invention operates in the following manner. The inlet tube 30 is connected to the faucet 22 by the use of the faucet connector 24. Water from the faucet 22 is introduced under pressure through water inlet tube 30 into the housing 50 through one of the pair of ports 40,42 (in FIG. 2 through port 40). The water so introduced is directed toward and strikes against leg 46 of the paddle wheel 44 causing it and the center shaft 43, to which it is fixedly attached, to rotate in the direction or path of the movement of the water. Rotation of the center shaft 43 is translated to the removable brush element 70 which likewise rotates. Excess water is removed from the toothbrush 10 through the other of the pair of ports (in FIG. 2 through port 42) and then through the drain tube 35 which may be placed in the sink or other suitable depository. Should the direction of rotation of the paddle wheel 44 and center shaft 43 be changed by changing the direction or path of movement of the water (i.e. by changing ports 40, 42 as the inlet and outlet ports), the direction of movement or rotation of brush element 70 will change. Specifically referring to FIG. 3, should first port 40 be the inlet and second port 42 the outlet, paddle wheel 46 and center shaft 43, and therefore the brush element, shall rotate clockwise as shown in FIG. 3, and should second port 42 be the inlet and first port 40 be the outlet, the paddle wheel 46 and center shaft 43, and therefore the brush element, shall rotate counterclockwise as shown in FIG. 3.

The toothbrush 10 with its rotating brush element 70 can be used for teeth cleaning and brushing as well as for gum massage or the like.

Having thus described the invention with particular reference to the preferred forms thereof, it will be obvious that various changes and modifications may be made thereon without departing from the spirit and scope of the invention as defined by the appended claims.

Wherefore, I claim:

1. A water powered rotary toothbrush adapted to rotate in either of two directions comprising:
   a housing having a center shaft and a pair of ports;
   said center shaft having a first end in said housing and a second end extending out of said housing, said center shaft being rotatable in either direction;

said pair of ports being axially aligned with respect to each other, and each port being located on an opposite side of said housing;

a paddle wheel connected to said center shaft and positioned near the first end of said center shaft and approximately equally spaced from each one of said pair of ports, said paddle wheel being rotatable with said center shaft;

a rotatable brush element removably attached to the second end of said center shaft; and means for introducing water into said housing through one of said pair of ports so as to strike said paddle wheel causing said center shaft, said paddle wheel and said brush element to rotate and in the same direction.

2. The water powered rotary toothbrush according to claim 1, wherein one of said pair of ports is an inlet port and the other of said pair of ports is an outlet port, said inlet and outlet ports are interchangeable for reversing the direction of rotation of said brush element.

3. The toothbrush of according to claim 2, wherein said means for introducing water into said housing include said inlet port and a flexible inlet tube for connecting said inlet port to a faucet of a sink.

4. The toothbrush of according to claim 3, wherein said inlet tube is attached to the faucet of the sink by flexible faucet connector.

5. The toothbrush of according to claim 2, wherein said outlet port is connected to a drain tube.

6. The water powered rotary toothbrush according to claim 1, wherein said paddle wheel includes a solid hub having an annular outer circumference and a plurality of paddle legs extending laterally outward from the outer circumference of said hub, wherein when one of said plurality of paddle legs is positioned basically perpendicular with respect to the axial direction of said pair of ports water entering through one of said pair of ports basically strikes only said one paddle leg thereby minimizing the amount of water needed to rotate said paddle wheel.

7. The water powered rotary toothbrush according to claim 6, wherein said hub is of a diameter at least two times greater than the radial extent of each of said plurality of paddle legs.

* * * * *